United States Patent [19]

Libbey

[11] 4,100,209

[45] Jul. 11, 1978

[54] SEPARATION OF ALKYL ALCOHOLS FROM ALKYLDIMETHYLAMINES

[75] Inventor: William J. Libbey, Ponca City, Okla.

[73] Assignee: Continental Oil Company, Ponca City, Okla.

[21] Appl. No.: 741,190

[22] Filed: Nov. 12, 1976

[51] Int. Cl.$^2$ .................... C07C 29/24; C07C 85/26
[52] U.S. Cl. ................... 568/918 D; 260/583 N
[58] Field of Search .................... 260/583 N, 643 D

[56] References Cited

U.S. PATENT DOCUMENTS

| 2,237,628 | 4/1941 | Olin et al. | 260/583 N |
| 2,527,017 | 10/1950 | Luten et al. | 260/583 N |
| 3,088,982 | 5/1963 | Feldman et al. | 260/643 D |
| 3,927,102 | 12/1975 | Chiou et al. | 260/583 N |

*Primary Examiner*—Joseph E. Evans
*Attorney, Agent, or Firm*—Bayless E. Rutherford, Jr.

[57] ABSTRACT

Alkyl alcohols are separated from alkyldimethylamines using an immiscible solvent mixture comprising a polar solvent (e.g. dimethylformamide) and a nonpolar solvent (e.g. hexane). The process is particularly useful for $C_{12-14}$ alcohols and $C_{12-14}$ alkyldimethylamines.

9 Claims, No Drawings

SEPARATION OF ALKYL ALCOHOLS FROM ALKYLDIMETHYLAMINES

FIELD OF THE INVENTION

The invention is in the general field of separating alkyl alcohols from alkyldimethylamines.

GENERAL BACKGROUND

Alkyldimethylamines, particularly wherein the alkyl group contains 10 to 14 carbon atoms, have a variety of commercial uses. For example they can be used per se as lube oil additives and as hardeners for epoxy resins. The quatenary ammonium salts are effective as germicides and are used in textile processing.

Alkyldimethylamines can be prepared from alcohols by processes which convert substantially all of the alcohol to the amine.

Alkyldimethylamines, also, can be prepared from alcohols by processes which give incomplete alcohol conversion. While there are advantages to this type of process there is the disadvantage that alkyldimethylamines having the same number of carbon atoms in the alkyl group as the alcohol from which it is prepared are difficult to separate by distillation. To illustrate this feature the boiling points of alcohols and corresponding alkyldimethylamines are given below.

| Boiling Points of Alcohols and Alkyldimethylamines | |
|---|---|
| Compound | Boiling Point ° C. |
| $n$-$C_{12}OH$ | 255–259° at 760 mm, 150° at 20 mm |
| $n$-$C_{12}NMe_2$ | 147–148° at 20 mm |
| $n$-$C_{14}OH$ | 167° at 15 mm |
| $n$-$C_{14}NMe_2$ | 159–161° at 11 mm |
| $n$-$C_{16}OH$ | 340° at 760 mm, 190° at 15 mm |
| $n$-$C_{16}NMe_2$ | 203° at 17 mm |

It is thus apparent that it would be desirable to have a technique for separating alcohols and alkyldimethylamines. My invention is directed to providing a solution to this problem.

PRIOR ART

A search of the prior art did not produce any references pertinent to the present invention.

German patent No. 1,202,261 teaches use of aqueous methanol or acetone in conjunction with paraffinic hydrocarbons to separate mixtures of higher weight alcohols and hydrocarbons. This is not considered pertinent to the present invention.

BRIEF SUMMARY OF THE INVENTION

Broadly stated, the present invention is directed to a method of separating a mixture of alkyl alcohols and alkyldimethylamines to give alkyl alcohols and alkyldimethylamines wherein the method comprises (a) contacting the mixture of alcohols and alkyldimethylamines with an effective amount of an immiscible solvent mixture comprising a polar solvent and a nonpolar solvent, (b) forming a polar phase containing alcohol and a nonpolar phase containing alkyldimethylamine, and (c) recovering the alcohol from the polar phase and recovering the alkyldimethylamine from the nonpolar phase.

In one aspect, the present invention is directed to a method for removing alcohols from a mixture of alcohols and alkyldimethylamines wherein the method comprises (a) contacting said mixture of alcohols and alkyldimethylamines with an effective amount of an immiscible solvent mixture comprising a polar solvent and a nonpolar solvent, (b) forming a polar phase containing a substantial amount of said alcohols and a nonpolar phase containing a substantial amount of said alkyldimethylamines and (c) removing the polar solvent and nonpolar solvent from the respective polar and nonpolar phases.

In another aspect, the present invention is directed to a method of enriching the alkyldimethylamine content of a mixture of alcohols and alkyldimethylamines wherein the method comprises the procedure described in the foregoing.

In a preferred embodiment the method is conducted on a continuous basis wherein the polar solvent and nonpolar solvent are fed countercurrently to each other and the mixture of alcohol and alkyldimethylamine is fed to the combined polar solvent and nonpolar solvent stream.

DETAILED DESCRIPTION

Suitable alkyldimethylamines for use in my process contain from 6 to 18 carbon atoms in the alkyl group. More suitably the alkyl group contains 10 to 14 carbon atoms, while preferably it contains 12 to 14 carbon atoms. The alkyl group can be straight or branched-chain. The alkyldimethylamines can include mixtures wherein the alkyl group conforms to the designated number of carbon atoms.

The alcohols which are present in the alcoholalkyldimethylamine mixture used in my process contain from 6 to 18 carbon atoms, more suitably from 10 to 14 carbon atoms, and preferably from 12 to 14 carbon atoms. The alkyl groups can be branched- or straight-chain. Mixtures of alcohols containing the designated number of carbon atoms are suitable. The alkyl group, or groups, of the alcohols can be different, i.e. number of carbon atoms, from the alkyl groups in the alkyldimethylamines.

The alkyldimethylamine-alcohol mixture can have an amine to alcohol ratio, on a volume basis, of about 98:2 to 2:98. On the same basis, preferably the amine to alcohol ratio is in the range of about 9:1 to 1:9.

Suitable polar solvents are dimethylformamide and 2-amino-2-methyl-1-propanol.

Any nonpolar solvent immiscible with the polar solvent is suitable. The more suitable nonpolar solvents are linear or cyclic saturated hydrocarbons containing five to nine carbon atoms. The preferred nonpolar solvents are linear saturated hydrocarbons containing five to seven carbon atoms.

The preferred ratio of polar to nonpolar solvent is in the range of about 0.9:1 to about 1.4:1 on a volume basis. Ratios of polar to nonpolar solvent in the range of about 4:1 to about 1:4 are suitable provided the solvents are still immiscible.

In conducting our process the ratio of solvent to solute on a volume basis is in the range of about 2:1 to about 50:1.

The temperature and pressure at which my process is conducted is not critical. Usually the process is conducted at ambient conditions.

The alcohol can be recovered from the polar solvent by distillation. Similarly the amine can be recovered from the nonpolar solvent by distillation.

In referring to removal of alcohols from the mixture of alcohols and alkyldimethylamines the term "substantial amount" as used herein and in the claim refers to greater than 50 percent by volume of that originally present.

In order to illustrate the nature of the present invention still more clearly the following examples will be given. It is to be understood, however, that the invention is not to be limited to the specific conditions or details set forth in these examples insofar as such limitations are specified in the appended claims.

EXAMPLE 1

This example illustrates my process with countercurrent extraction using a one inch diameter 7.5 ft. long York-Scheibel column containing 26 settling sections.

The amine-alcohol mixture was a 77:23 mixture (volume) of dodecyldimethylamine ($C_{12}NMe_2$) and 1-dodecanol.

Dimethylformamide (DMF) was the polar solvent, while hexane was the nonpolar solvent. The DMF was fed to the column at the top, the hexane at the bottom, while the amine-alcohol mixture was fed to the middle of the column. The temperature was 22°–25° C. The composition of the product was determined by GLC (gas liquid chromatography). The other process conditions and results are shown in Table I.

TABLE I

| Run No. | Feed Rate (ml/hr) | Stirring Rate (RPM) | Ratio of DMF to Hexane | Continuous Phase | Total Solvent to Solute Ratio | GC Area % | |
|---|---|---|---|---|---|---|---|
| | | | | | | $C_{12}NMe_2$ | $C_{12}OH$ |
| A-hexane-top | 950 | 650 | 0.95:1 | DMF | 10:1 | 97.9 | 2.1 |
| A-DMF-bottom | 950 | 650 | 0.95:1 | " | 10:1 | 0 | 100 |
| B-hexane-top | 1150 | 800 | 1.4:1 | " | 11:1 | 99.0 | 1.0 |
| B-DMF-bottom | 1150 | 800 | 1.4:1 | " | 11:1 | 0 | 100 |
| C-hexane-top | 1110 | 800 | 1:1 | hexane | 11:1 | 99.0 | 1.0 |
| C-DMF-bottom | 1110 | 800 | 1:1 | " | 11:1 | 2.1 | 97.9 |
| D-hexane-top | 1200 | 800 | 1.35:1 | " | 11:1 | 99.5 | 0.5 |
| D-DMF-bottom | 1200 | 800 | 1.35:1 | " | 11:1 | 5.7 | 94.3 |

EXAMPLE 2

Runs C and D of Example 1 were repeated except that tetradecanol was added to the feed in addition to the dodecanol and dodecyldimethylamine. Results were obtained similar to those shown in Table I. The alcohol mixture separated as efficiently from $C_{12}NMe_2$ as $C_{12}OH$ alone had separated.

EXAMPLE 3

This example illustrates the following: (a) batch extraction and (b) relative effectiveness of dimethylformamide (DMF) and 2-amino-2-methyl-1-propanol (AMP) as the polar solvent.

The procedure was as follows: Added 6 ml of hexane, 6 ml of polar solvent, 1 ml of dodecanol and 1 ml of dodecyldimethylamine to a separatory funnel. The funnel was shaken and the phases allowed to separate (23° C.). The polar and nonpolar phases were analyzed by GLC. The results are shown in Table II.

TABLE II

| Polar Solvent | Separation Factor* | w/o of Total $C_{12}OH$ in the Polar Phase | w/o of Total $C_{12}NMe_2$ in the Nonpolar Phase |
|---|---|---|---|
| DMF | 5.46 | 57% | 81% |
| AMP | 7.06 | 82% | 61% |

$$^*\text{Separation Factor} = \frac{k\, C_{12}NMe_2}{k\, C_{12}OH} = \frac{\frac{\text{Concentration of } C_{12}NMe_2 \text{ in nonpolar solvent}}{\text{Concentration of } C_{12}NMe_2 \text{ in polar solvent}}}{\frac{\text{Concentration of } C_{12}OH \text{ in nonpolar solvent}}{\text{Concentration of } C_{12}OH \text{ in polar solvent}}}$$

Inasmuch as separation factor is a measure of the efficiency of separation, the above data shows AMP is slightly more effective than DMF in the separation.

Thus, having described the invention in detail, it will be understood by those skilled in the art that certain variations and modifications may be made without departing from the spirit and scope of the invention as defined herein and in the appended claims.

I claim:

1. A process for removing $C_6$–$C_{18}$ alkanols from a mixture of $C_6$–$C_{18}$ alkanols and $C_6$–$C_{18}$ alkyldimethylamines wherein the process comprises (a) contacting said mixture of alkanols and alkyldimethylamines with an effective amount, in the range of about 2:1 parts to about 50:1 parts per volume of said mixture, of an immiscible solvent mixture comprising a polar solvent selected from the group consisting of dimethylformamide, 2-amino-2-methyl-1-propanol, and mixtures thereof, and a nonpolar solvent, said polar solvent and said nonpolar solvent being present in the range of about 4:1 to about 1:4, on a volume basis, and still being immiscible, (b) forming a polar phase containing a substantial amount of said $C_6$–$C_{18}$ alkanols and a nonpolar phase containing a substantial amount of said $C_6$–$C_{18}$ alkyldimethylamines, (c) separating said polar phase and said nonpolar phase, and (d) removing the polar solvent and nonpolar solvent from the respective polar and nonpolar phases.

2. The process of claim 1 wherein the nonpolar solvent is a linear or cyclic saturated hydrocarbon containing five to nine carbon atoms.

3. The process of claim 2 wherein the alkyldimethylamine-alcohol mixture has an amine to alcohol ratio, on a volume basis, of about 98:2 to 2:98.

4. The process of claim 3 wherein the term substantial amount refers to greater than 50 percent by volume of that originally present.

5. The process of claim 4 wherein the alcohols contain 10 to 14 carbon atoms and the alkyl group of said alkyldimethylamine contains 10 to 14 carbon atoms.

6. The process of claim 5 wherein the ratio of polar to nonpolar solvent is in the range of about 0.9:1 to about 1.4:1 on a volume basis.

7. The process of claim 1 wherein it is conducted on a continuous basis wherein the polar solvent and nonpolar solvent are fed countercurrently to each other and the mixture of alcohols and alkyldimethylamines is fed to the combined solvent and nonpolar solvent stream.

8. The process of claim 3 wherein it is conducted on a continuous basis wherein the polar solvent and nonpolar solvent are fed countercurrently to each other and the mixture of alcohols and alkyldimethylamines is fed to the combined solvent and nonpolar solvent stream.

9. The process of claim 6 wherein it is conducted on a continuous basis wherein the polar solvent and nonpolar solvent are fed countercurrently to each other and the mixture of alcohols and alkyldimethylamines is fed to the combined solvent and nonpolar solvent stream.

* * * * *